(12) United States Patent
Rumpler et al.

(10) Patent No.: US 11,439,520 B2
(45) Date of Patent: Sep. 13, 2022

(54) ORTHOPEDIC DEVICE

(71) Applicant: Otto Bock Healthcare Products GmbH, Vienna (AT)

(72) Inventors: Julian Rumpler, Katzeldorf (AT); Kay Bodenstein, Vienna (AT); Juan Pablo Mejia Nino, Vienna (AT)

(73) Assignee: OTTO BOCK HEALTHCARE PRODUCTS GMBH

( * ) Notice: Subject to any disclaimer, the term of this patent is extended or adjusted under 35 U.S.C. 154(b) by 115 days.

(21) Appl. No.: 16/413,215

(22) Filed: May 15, 2019

(65) Prior Publication Data

US 2019/0298550 A1 Oct. 3, 2019

Related U.S. Application Data

(63) Continuation-in-part of application No. PCT/EP2019/050296, filed on Jan. 8, 2019.

(30) Foreign Application Priority Data

Jan. 8, 2018 (DE) .......................... 102018100252.1

(51) Int. Cl.
*A61F 2/74* (2006.01)
*A61F 2/68* (2006.01)
(Continued)

(52) U.S. Cl.
CPC ................ *A61F 2/68* (2013.01); *A61F 2/604* (2013.01); *A61F 2/605* (2013.01); *A61F 2/64* (2013.01);
(Continued)

(58) Field of Classification Search
CPC .. A61F 2/68; A61F 2/604; A61F 2/605; A61F 2/64; A61F 5/01; A61F 5/0102; A61F 5/00; A61F 5/0123; A61F 5/0125; A61F 2002/5038; A61F 2002/5039; A61F 2002/5006; A61F 2002/745; A61F 2002/748; A61F 2002/50003;
(Continued)

(56) References Cited

U.S. PATENT DOCUMENTS 2,657,393 A 11/1953 Haller
4,578,082 A * 3/1986 Sen-Jung .................. A61F 2/68
623/26

(Continued)

FOREIGN PATENT DOCUMENTS

DE 20306821 U1 7/2003
DE 102009004950 A1 7/2010
(Continued)

OTHER PUBLICATIONS

Russian Patent Office; Office Action; RU 2020123528/14; dated Dec. 30, 2021; 2 pages.

*Primary Examiner* — Brian A Dukert
(74) *Attorney, Agent, or Firm* — Holland & Hart LLP

(57) ABSTRACT

An orthopedic device with a hydraulic damping device, a valve with a valve seat and a valve body that is subjected to a closing force. The closing force is applied via a valve spring that is pre-loaded towards the valve seat. A fluid connection between the hydraulic damping device and the valve seat is provided. The valve features an adjustment device for adjusting the preload of the valve spring.

17 Claims, 6 Drawing Sheets

(51) Int. Cl.
*A61F 2/64* (2006.01)
*A61F 5/01* (2006.01)
*A61F 2/60* (2006.01)
*A61F 2/66* (2006.01)
*A61F 2/50* (2006.01)
*A61F 2/70* (2006.01)

(52) U.S. Cl.
CPC .......... *A61F 5/0102* (2013.01); *A61F 2/6607* (2013.01); *A61F 2/74* (2021.08); *A61F 2/748* (2021.08); *A61F 2002/5003* (2013.01); *A61F 2002/5006* (2013.01); *A61F 2002/5033* (2013.01); *A61F 2002/607* (2013.01); *A61F 2002/6854* (2013.01); *A61F 2002/701* (2013.01); *A61F 2002/702* (2013.01); *A61F 2005/0158* (2013.01); *A61F 2005/0169* (2013.01)

(58) Field of Classification Search
CPC ........ A61F 2002/5036; A61F 2002/701; A61F 2002/607; A61F 2002/608; A61F 2005/0169; A61F 2/74; A61F 2/748; A61F 2002/5033; B25J 9/0006; A61H 3/00; A16F 9/00; A16F 9/44; A16F 9/446; A16F 9/50
See application file for complete search history.

(56) References Cited

U.S. PATENT DOCUMENTS

| | | | |
|---|---|---|---|
| 5,888,212 A * | 3/1999 | Petrofsky | F16F 9/46 |
| | | | 623/24 |
| 6,706,074 B1 * | 3/2004 | Chen | A61F 2/68 |
| | | | 623/44 |
| 6,899,313 B2 * | 5/2005 | Carrillo | F16K 31/0665 |
| | | | 123/90.12 |
| 8,814,948 B2 * | 8/2014 | Pusch | A61F 2/64 |
| | | | 623/24 |
| 9,540,807 B2 * | 1/2017 | Ueno | E04H 9/02 |
| 9,763,809 B2 * | 9/2017 | Palmer | A61F 2/70 |
| 10,085,857 B2 | 10/2018 | Boender et al. | |
| 2006/0259153 A1 * | 11/2006 | Harn | A61F 2/644 |
| | | | 623/44 |
| 2008/0228287 A1 | 9/2008 | Ninomiya | |
| 2018/0256380 A1 | 9/2018 | Pusch et al. | |

FOREIGN PATENT DOCUMENTS

| | | |
|---|---|---|
| DE | 102016202287 A1 | 8/2016 |
| EA | 19408 B1 | 3/2014 |
| RU | 47732 U1 | 9/2005 |
| WO | 2010/031766 A1 | 3/2010 |
| WO | 2017050552 A1 | 3/2017 |

* cited by examiner

ORTHOPEDIC DEVICE

CROSS REFERENCE

The present application is a continuation in part of International Patent Application No. PCT/EP2019/050296, filed Jan. 8, 2019, titled "Orthopedic Device", which claims priority to German Patent Application No. 102018100252.1, filed Jan. 8, 2018, titled "Orthopedic Device", the disclosures of which are incorporated herein in their entireties by this reference.

TECHNICAL FIELD

The present disclosure relates to an orthopedic device with a hydraulic damping device, which has a valve with a valve seat and a valve body that is subjected to a closing force, the closing force being applied via a valve spring that is pre-loaded towards the valve seat, and a fluid connection between the hydraulic damping device and the valve seat.

BACKGROUND

Orthopedic devices, especially prostheses or orthoses, may be equipped with a hydraulic damping device that features a piston and a cylinder, wherein the piston generally divides the cylinder into an extension chamber and a flexion chamber when the hydraulic damping device is arranged on a joint. Depending on the extension or flexion movement, hydraulic fluid moves from one chamber into the other. In another arrangement, the two chambers are described as a compression chamber and an expansion chamber. With hydraulically damped joint devices, adjustable valves are often designed as flow-control valves, by means of which the resistances in the respective flow channels can be adjusted, either variably or statically. The flow-control valves may be manually adjustable or adjustable by way of a motor. Furthermore, non-return valves are arranged in hydraulic damping devices, wherein the non-return valves block the f flow depending on the flow direction of the fluid. To keep the valve body in the desired position, these valves are generally spring-loaded, wherein the spring pre-loads the valve body in the valve seat. To enable the hydraulic fluid to flow through the non-return valve, a pressure must act in the opposite direction to the spring force, thereby causing the valve body to be raised up off of the valve seat. Hydraulic damping devices sometimes contain so-called safety valves, which open when a maximum permitted pressure is exceeded in order to protect the orthopedic device, especially the hydraulic damping device, from mechanical damages or the patient from injury. The safety valve is an overload safety device that opens when a predetermined pressure is reached. Installation space is often restricted, in particular with orthopedic devices that feature a hydraulic damping device. Nevertheless, strong forces must be applied via small valve springs, which either directly or indirectly exert a pre-tension force on the valve body. If the valve spring is configured as a mechanical helical spring or coiled spring, it is particularly problematic that there is a broad range of manufacturing tolerances, meaning that a desired valve-opening force can only be achieved by testing a large number of valve springs.

DE 203 06 821 U1 relates to an artificial knee joint arrangement with a prosthesis socket that is connected to an upper part of the joint arrangement. The upper part is connected via a multi joint arrangement to a lower part in such a way that it can be swivelled. A lower leg tube is connected to the lower part such that it can be swivelled about an axis. A hydraulic cylinder unit is arranged inside the lower part, the cylinder unit being coupled with the upper part via a connecting element. If the upper part is swivelled relative to the lower part, a piston is displaced inside the hydraulic cylinder unit. A valve arrangement is arranged in a connection channel between two chambers inside the cylinder unit; a displacement of the lower part relative to the lower leg part can be activated by way of the valve arrangement, such that the flow of hydraulic oil between an upper oil chamber and a lower oil chamber is stopped if the lower leg tube is swivelled relative to the lower part.

SUMMARY

The object of the present disclosure is therefore to provide an orthopedic device where a desired valve-opening force is always available.

According to the present disclosure, this object is achieved by the advantageous configurations and embodiments disclosed in the description and the figures.

The orthopedic device according to the present disclosure, with a hydraulic damping device, which has a valve with a valve seat and a valve body that is subjected to a closing force, the closing force being applied via a valve spring that is pre-loaded towards the valve seat, and a fluid connection between the hydraulic damping device and the valve seat, provides that the valve features an adjustment device for adjusting the pre-tension of the valve spring. Whereas pressure relief valves from the prior art feature a fixed setting and a large variation in the respective opening forces due to various degrees of spring stiffness, the device according to the present disclosure renders it possible to provide a constantly uniform closing force of the valve body, even if the degrees of stiffness of the respective valve springs are different; as a result, the quality of the orthopedic device remains the same, regardless of the manufacturing tolerances of the valve spring. It is also possible to customize the orthopedic device to a respective user or patient. For instance, with orthopedic devices such as lower limb orthoses or prostheses, the required closing force may vary according to the body weight or the load weight on the respective joint. A light patient may require a small spring force to open the valve, so that the joint device yields when a certain load is present, whereas a higher closing force can be set for a heavier patient or a greater load, for example if the patient carries heavy loads. The adjustment of the closing force by changing the preload of the valve spring also allows the valve to be adjusted to fit different orthopedic devices with different purposes and different model sizes, for example.

An embodiment of the present disclosure proposes that the adjustment device comprise a threaded drive or screw drive, by means of which the valve spring can be pre-loaded. The valve spring itself may be designed to be a mechanical spring, such as a coiled spring or a helical spring, and either push or pull the valve body into the valve seat, especially by way of a compressive force or a tensile force. It is also possible to provide alternative valve springs, such as an elastomer element or a pre-loaded, compressible volume, such as a bubble filled with gas. The valve body can be in direct contact with the valve spring; alternatively, the closing force of the valve body may be applied to the valve body via a support element or a preferably incompressible fluid in order to press the valve body into the valve seat.

The adjustment device may comprise a valve spring holder that is coupled with the valve spring, wherein the valve spring holder is mounted in a housing and a first thread is configured on it, the first thread engaging with a second thread, which is arranged in the housing. The adjustment device may be used in combination with at least the valve spring and the valve body, along with the valve spring holder, in a separate housing and designed as a module. Alternatively, the housing may form part of the housing of the orthopedic device, for example a flow channel, inside of which an inner thread is arranged or configured, wherein the inner thread can engage with a thread of a valve spring holder, in which the valve spring either pre-loads or slackens. For instance, the valve spring holder may be designed as a pin, a sleeve or a similar receiving device, on or in which the valve spring is arranged and by means of which the valve spring can be pre-loaded or slackened. Depending on the direction in which the adjustment device is moved, the valve spring is either pre-loaded or slackened via the screw drive.

The valve body can be pre-loaded with a pre-tension force towards to the valve seat, wherein the pre-tension force can be virtually any strength. Depending on which closing force must be provided to protect the hydraulic system or to adjust the hydraulic damping device to the respective patient or the respective operating condition, the pre-tension force can be set and adjusted via the adjustment device. The pre-tension force is preferably steplessly or infinitely adjustable so as to offset any deviations or variations in the manufacturing of the springs and to enable the execution of precise adjustments to the user and/or the purpose of use. The fact that it is infinitely adjustable means that variations can be reduced to a considerable extent and the pre-tension force set to the nominal value with very small deviations. The deviations from the nominal value are preferably lower than 10%, especially preferably lower than 5%, for instance if the nominal value is 9 kN, the pre-tension force can be set with an accuracy of ±0.4 kN.

The adjustment device may feature adjustment markings so the user or the orthopedic technician can set the desired closing force with the aid of the adjustment markings. Following the installation of the spring, a test force can be applied to the valve body. If the valve opens prior to reaching the set test force, the preload increases; if the valve does not open, the spring preload is reduced, thereby also reducing the closing force. Via a gradation of the respective applied test force and the application of the respective adjustment marking upon reaching the desired test force, the relevant adjustment marking or markings can be individually applied for each spring.

The adjustment device preferably has a positive-locking element, which can be used to activate the adjustment device. For instance, as a slot, cross-slot, polygonal profile, torx insert, hexagon socket or a corresponding projection, the positive-locking element may enable the transmission of a force from a tool or a motor drive to the adjustment device.

An embodiment of the present disclosure provides that the adjustment device comprises a motor drive and a control device that is coupled with the motor drive for controlling the motor drive. Specifically, the drive is designed to be an electromotive drive. Alternative motor drive devices for adjusting the preload of the valve spring are possible and proposed. By activating or deactivating the drive, without requiring direct access to the adjustment device, the motor drive can be used to carry out the desired adjustment in the respective desired direction.

The orthopedic device preferably features an operating element, which is coupled with the control device, and/or a communication center for controlling the motor drive so that the adjustment of the respective spring preload can be comfortably achieved via a remote control or an operating element on the orthosis, the prosthesis, the wheelchair or another orthopedic device.

An embodiment of the present disclosure provides that the orthopedic device comprise at least one sensor, which is coupled with the control device. The sensor can be used to supply the control device with user data or usage data of the orthopedic device in order to be able to adjust the spring preload and therefore the closing pressure or the pressure at which the valve body opens the valve. By way of a direct adjustment by the user of the damping device or an orthopedic technician via a manual adjustment or a motorized adjustment by means of an interface or an operating element, it is possible to have an adjustment automatically executed actively via the sensor for every state of use or for a special activity or for any changes in the user. For particular activities such as sports and carrying heavy objects or for special functions such as walking uphill or going downstairs, it may be practical to set certain closing pressures or limits to ensure that the hydraulic system does not suffer any damages during load peaks, or to prevent forces of too great a magnitude from being transferred to the patient via the prosthesis or orthosis device. Upon reaching the pressure limit, the respective joint or the respective orthopedic device yields: for lower limb joints, this occurs primarily upon a flexion of the knee or an ankle joint; for an ankle joint, this also occurs during an extension movement.

An active control using a control device, which adjusts the preload depending on at least one sensor value, can enable an improved customization and adjustment to the patient or the relevant activity.

An embodiment of the present disclosure proposes that the control device be configured to determine the body weight and/or a value of a parameter of a movement by means of at least one sensor; to calculate at least one control parameter for the drive from the determined value or values; and to automatically activate the drive to adjust the preload of the valve spring. In particular, the weight load can be measured, for instance via an axial force sensor, as can accelerations, torques or spatial positions; such measurements are used as a basis for the automatic adjustment of the valve.

Alternatively or in addition to a valve spring holder, which is mounted such that it can be adjusted, the adjustment device may be designed as an adjustable valve seat, in particular a valve seat that can be screwed and unscrewed and is situated in a piston or another component of the orthopedic device. The valve seat, against which the valve body is pressed by the valve spring, may comprise at least one positive-locking element, such as a hole, projection, slot or similar, by way of which the position of the valve seat relative to a counter bearing of the valve spring can be adjusted using a tool or by hand without a tool, for instance by using a screw thread to adjust and, if necessary, change the spring preload.

BRIEF DESCRIPTION OF THE DRAWINGS

Illustrative embodiments of the present disclosure are explained in more detailed below with reference to the attached figures, in which.

DETAILED DESCRIPTION

Figure 1:
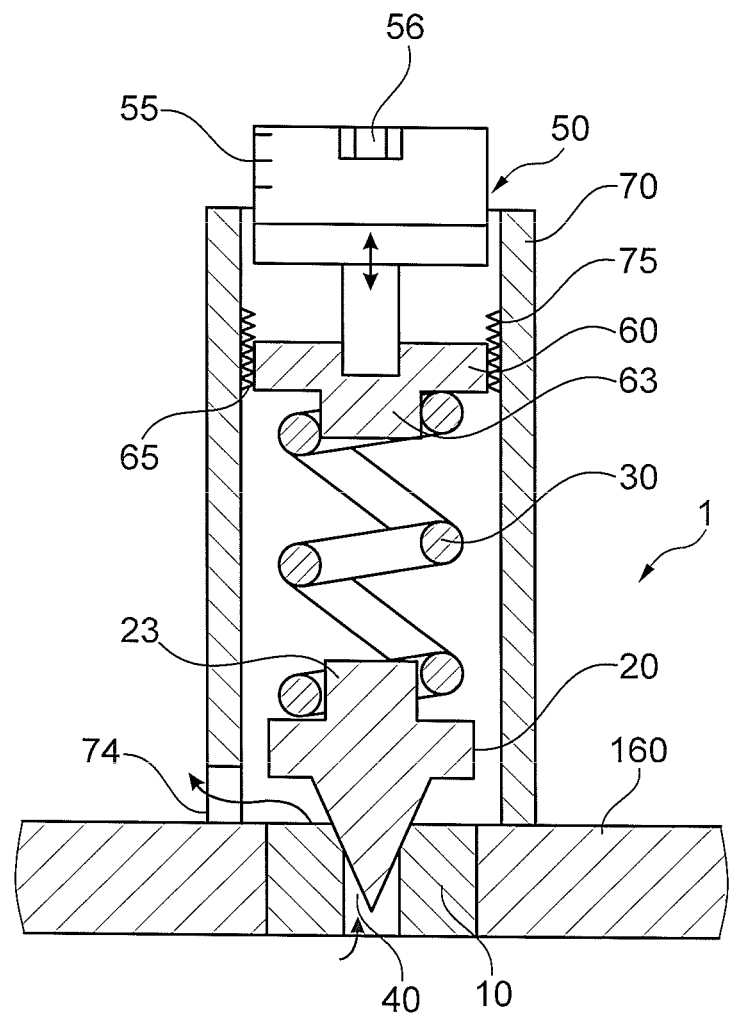
FIG. 1 is a schematic sectional view of a valve in accordance with the present disclosure.

FIG. 1 shows a schematic sectional view of a valve 1 with a valve seat 10, which is arranged in a part of a hydraulic damping device or another hydraulic system. In the example of the embodiment shown, the valve seat 10 is arranged inside a hydraulic piston 160, which will be described in more detail later. The valve seat 10 features a through-flow bore 40 or a passage that connects a high-pressure side to a low-pressure side. The passage 40 is sealed by a valve body 20. In the example of the embodiment shown, the valve body 20 features a conical tip, which protrudes into the passage 40 and seals it. Bevelled contact surfaces may be configured in the valve seat 10 in order to increase the contact surface of the valve body 20 on or in the valve seat 10. Via a spring 30, which is designed as a helical spring or a coiled spring in the example of the embodiment shown, the valve body 20 is subjected to a pre-tension force towards the valve seat 10 The valve body 20 features a projection or bolt-like protrusion 23, around which the helical spring is arranged 30. The protrusion 23 acts as a guide for the helical spring 30.

The helical spring 30 and the valve body 20 are guided in a sleeve 70 that is arranged on the piston 160. The sleeve 70 may form part of the piston 160 or be fixed to it. The sleeve 70 encloses the valve seat 10, the valve body 20 and the spring 30, and features an outlet 74, through which the hydraulic fluid or pneumatic fluid can leave the high-pressure side through the passage 40 when the valve is open. A valve spring holder 60 is arranged inside the sleeve 70, wherein the valve spring holder also comprises a bolt-like ledge 63, around which the helical spring 30 is mounted. On its outer side, the valve spring holder 60 features a thread 65 that engages with an inner thread 75 on the inner wall of the sleeve 70. Via the threads 65, 75, it is possible to compress or slacken the spring 30 by twisting the valve holder 60 in one direction or the other. If the valve spring holder 60 is shifted towards the valve body 20, the spring 30 is compressed and the closing force, with which the valve body 20 is pushed against the valve seat 10 and seals the passage 40, increases. If the valve spring holder 60 is shifted away from the valve body 20, the spring 30 slackens and the closing pressure decreases. This means that only a low pressure is required on the high-pressure side to raise the valve body 20 up off the valve seat 10 and open the passage 40 so that hydraulic fluid and/or pneumatic fluid can enter flow through from the high-pressure side and escape through the outlet 74. The outlet 74 can be coupled with an expansion tank, the high-pressure side or a connection line to the rest of the hydraulic system.

A non-circular recess is arranged centrally inside the valve spring holder 60; a correspondingly shaped pin of an adjustment device 50 engages with the recess. On the side of the adjustment device 50 that is facing away from the valve spring holder 60 there is a positive-locking element 56 in the form of a hexagon socket recess, into which a correspondingly shaped tool can be inserted. A twisting of the adjustment device 50 in one direction or the other causes, via the positive-locking coupling with the valve spring holder 60, a slackening or an increase in the preload of the valve spring 30. Markings 55 are provided on the outer side of the adjustment device 50, which can be used by the person conducting the adjustment to recognize to what extent a preload has been conducted. The markings can be used to determine a gradation of the preload, such that the pretension force can be adjusted in a controlled manner not only in qualitative terms but also in quantitative terms.

Figure 1B:
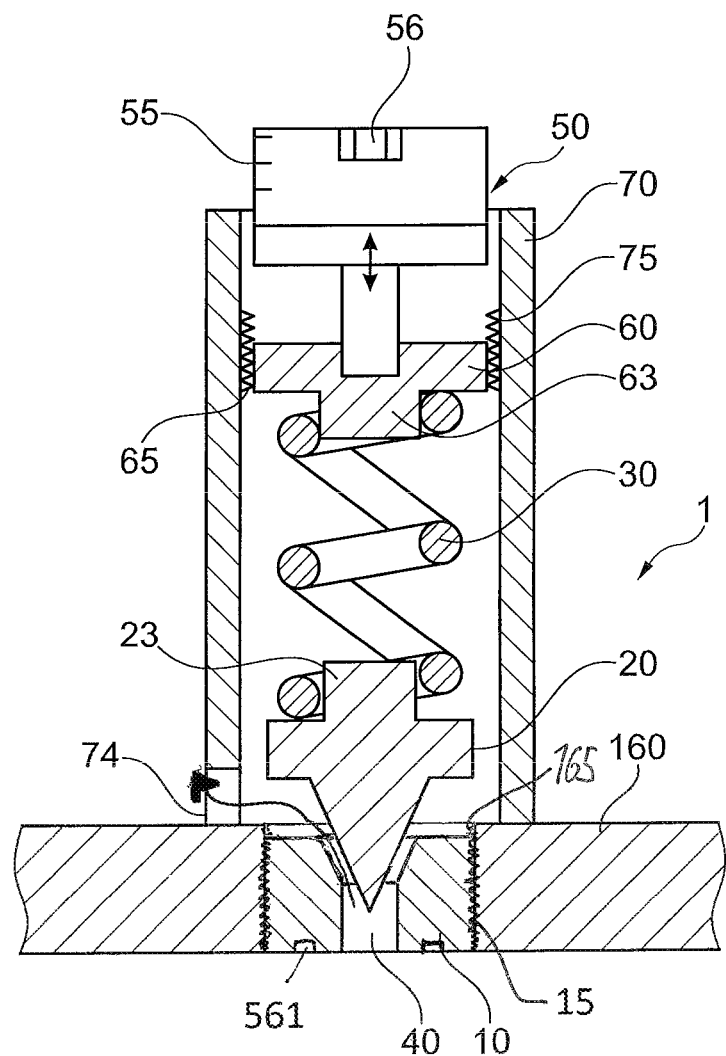
FIG. 1b is a variation of the embodiment shown in FIG. 1 with an adjustable valve seat.

FIG. 1b shows a variation of FIG. 1, in which the valve seat 10 is screwed into the hydraulic piston 160. An outer thread 15 is provided on the outer side of the valve seat 10, the outer thread being inserted along with an inner thread 165 in a bore inside the hydraulic piston 160 or another device. Positive-locking elements 561 are arranged or configured on the lower side of the valve seat 10, which may be made of a different material to the piston 160; via the positive-locking elements, it is possible to shift the valve seat 10 towards the valve body 20 using an appropriate tool. If the valve seat 10 is screwed in towards the valve body 20, the distance between the valve spring holder 60 and the contact surface for the conical tip of the valve body 20 reduces to such an extent that, when closed, the spring preload in the valve spring 30 is greater. In the state depicted, the valve body 20 is raised up off of the valve seat 10, such that a passage 40 from the lower side of the piston 160 emerges in a through-feed gap between the valve body 20 and the valve seat 10. This is illustrated by the arrow; the medium, which is a hydraulic medium in the case of a hydraulic piston 160, flows through the outlet 74. In the example of an embodiment shown, both the valve spring holder 60 and the valve seat 10 are adjustably mounted in the sleeve 70 or the piston 160, so that the valve features two adjustment devices, by way of which the preload of the valve spring 30 can be adjusted. The first adjustment device 50 is, for example, the tool or the handle or the head with the positive-locking element 56; the second adjustment device is the adjustable valve seat 10 with the positive-locking elements 561 and a device—not depicted—which engages with the positive-locking elements 561 and enables an adjustment of the preload of the valve spring 30.

Figure 1C:
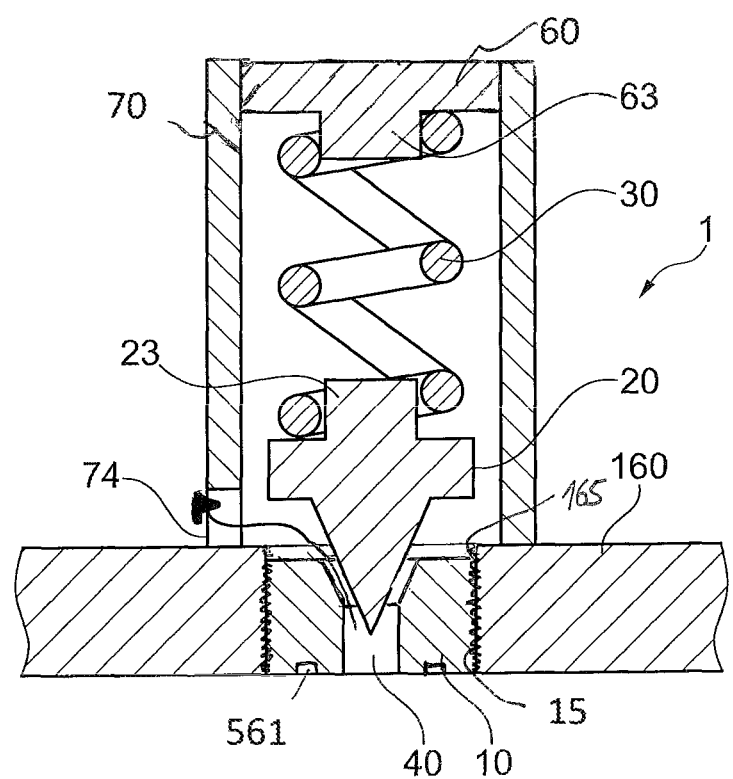
FIG. 1c is a variation of the embodiment shown in FIG. 1b.

Another variation of the present disclosure is shown in FIG. 1c, which comprises just one adjustment device instead of two, namely an adjustable valve seat 10. The valve spring holder 60 is fixed to the sleeve 70 such that it cannot be adjusted, for example it is secured by bolts, fixed by screws or welded. By twisting the valve seat 10 in and out, the preload of the valve spring 30 changes, either increasing or decreasing. Here, the valve seat 10 is also designed as a separate element and screwed into the piston 160, a housing or similar. By way of the outer thread 15 and the inner thread 165 of the valve seat 10, as shown in FIG. 1b, the preload is infinitely adjustable. The valve seat 10 is mounted on the valve seat accommodation, i.e. a piston or a housing, such that it can be adjusted, in particular screwed in, in or against the direction of action of the valve spring 30.

Figure 2:
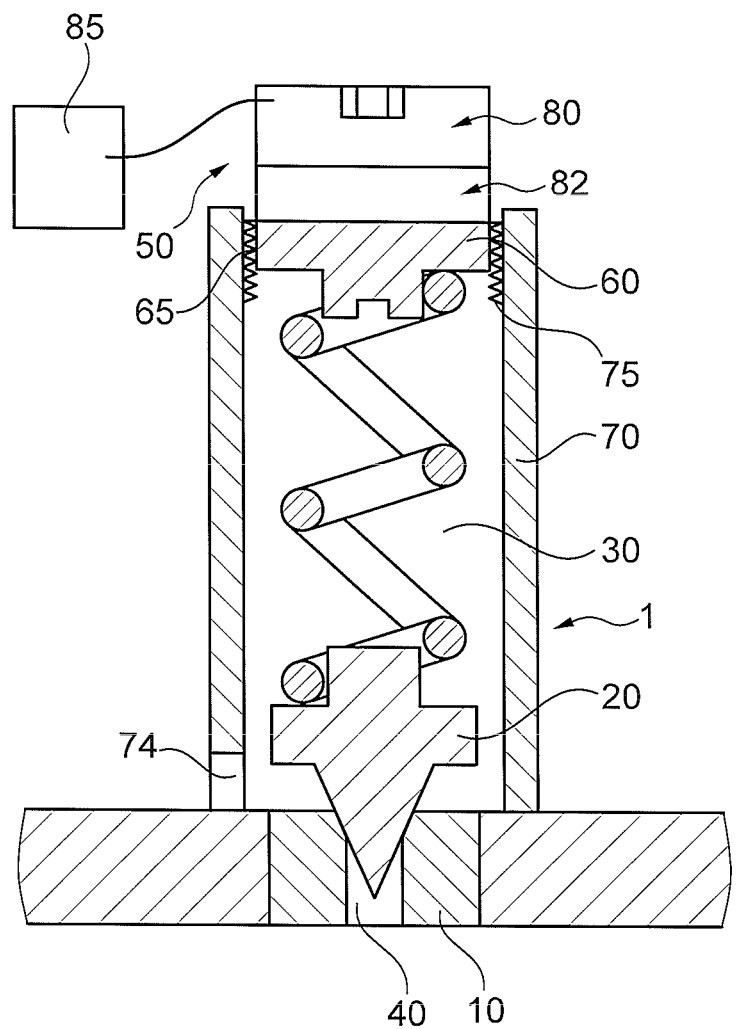
FIG. 2 is a variation of the embodiment shown in FIG. 1 with a motorized adjustment device.

FIG. 2 shows a variation of the valve arrangement according to FIG. 1, wherein a motorized adjustment device 50, rather than a mechanical, manually operated adjustment device 50, is coupled via a tool with the valve spring holder 60. The basic mechanical structure with the valve seat 10, valve body 20, pre-loaded spring 30 and the preload via the threads 65, 75 remains unchanged. A drive 80, especially an electromotive drive 80, is arranged at the end of the valve spring holder 60 that is situated away from the valve body 20, the drive being coupled with the valve spring holder 60 via a thread 82. The motor drive 80 is coupled with a control device 85, which in turn may be coupled with at least one sensor, an operating device or a communication device in order to drive the motor 80 via corresponding control signals in one direction or the other. By twisting the valve spring holder 60 inside the sleeve 80, the screw drive effects an axial shift of the valve spring holder 60 towards or away from the valve body 20, thereby causing an increase in the preload or a slackening of the spring 30.

The thread 82 may be arranged or configured in particular as a spindle drive, so the motor 80 itself remains stationary and only drives the thread 82 via a drive shaft in order to effect a compression or slackening of the spring 30 via the valve spring holder 60. Other adjustment devices 50 may also be provided, for instance purely linear adjustment devices, which work without a thread transmission. The control device 85 may be coupled with the drive 80 via a cable; however, a cable-free coupling is also possible.

Figure 3:
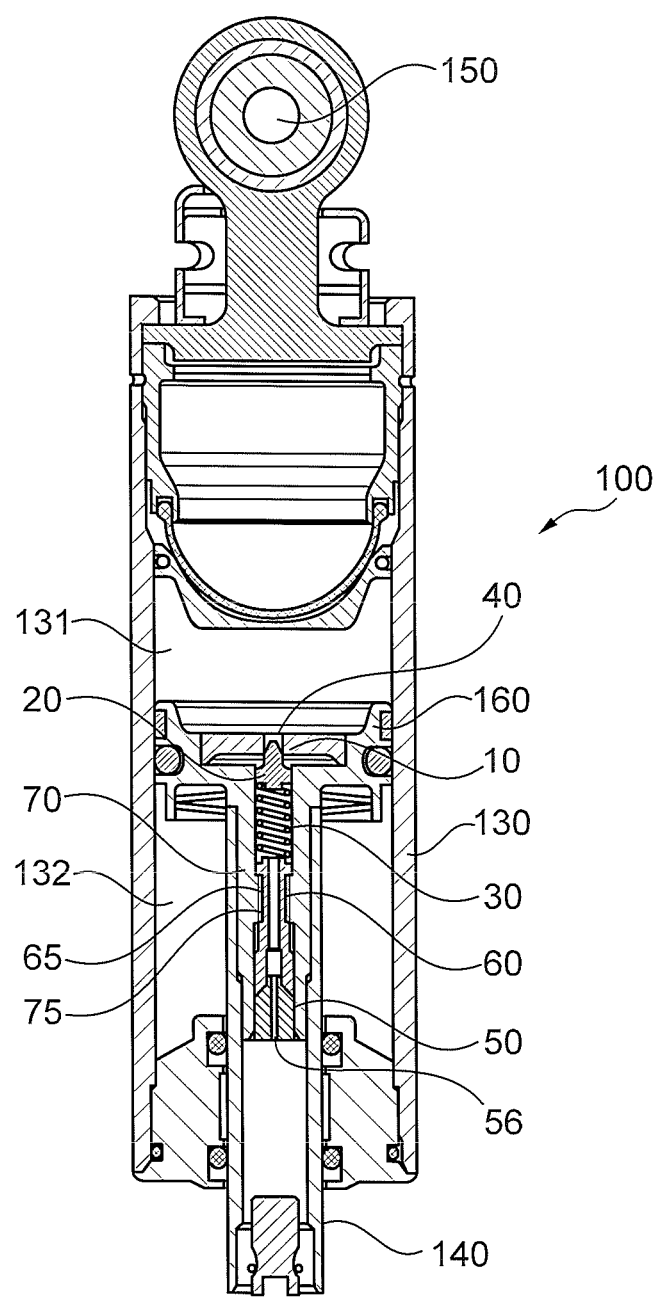
FIG. 3 is a sectional view through a hydraulic damper with the valve in accordance with the present disclosure.

FIG. 3 depicts a sectional view of a hydraulic system in the form of a hydraulic damping device 100, to which the control device 85 from FIG. 2 can be allocated. The hydraulic actuator 100 has a housing 130, to which a bearing accommodation 150 is fixed for attaching the housing to, for example, an orthosis or prosthesis. A cylinder is configured inside the housing 130, wherein a hydraulic piston 160 is arranged inside the cylinder on a piston rod 140 such that it can be moved in the longitudinal direction. The hydraulic piston 160 separates a flexion chamber 131 from an extension chamber 132. An additional bearing device may be provided at the end of the piston rod 140 that faces away from the piston 160, in the same way as the bearing accommodation 150 on the housing 130, so as to be able to fix the hydraulic actuator 100 on, for instance, a lower part or an upper part of an orthosis or prosthesis.

A valve seat 10 is configured inside the piston 160, which can be moved in the longitudinal direction, wherein the valve body 20 is inserted in the valve seat. On the piston rod side of the piston 160, the valve body 20, the cross-section of which is circular, is inserted in a recess, especially a cylindrical bore, and loaded via the valve spring 30 towards the valve seat 10. The valve spring holder 60 is also arranged inside the sleeve 70, which forms part of the piston 160 in the example of the embodiment shown and surrounds the bore, wherein the valve spring holder features the outer thread 65 on its outer side, the outer thread being designed to match an inner thread 75 in the sleeve 70. The piston rod 140 can be utilized to execute a manual adjustment of the spring preload via an adjustment device 50, which comprises a positive-locking element 56 in the form of a non-circular or angular recess at its back end; this is achieved by shifting the adjustment device 50 and thus also valve spring holder 60, which can be axially adjusted by way of the screw drive. Depending on the direction of rotation, the spring 30 is slackened or compressed. If an overload peak emerges in the flexion chamber 131 in the course of the activation of the hydraulic damper 100 during a flexion movement, the valve 1 opens by way of the valve body 20 being pushed out of the valve seat 10 by the spring 30 against the spring force, such that the passage 40 is opened and hydraulic fluid can flow from the flexion chamber 131, through channels—not depicted—and into the extension chamber 132. In principle it is also possible to interchange the flexion chamber 131 and the extension chamber 132, such that in the event of high pressure during an extension movement the valve 1 can be opened in a controlled manner. Due to the adjustability of the pre-loaded spring 30, it possible on the one hand to adjust the opening pressure of the valve body 20 more precisely, and on the other hand to react to different activities, different walking situations or changes in the user of the orthopedic device that occur during use via an adjustment of the preload, and to execute a corresponding adjustment.

Figure 4:
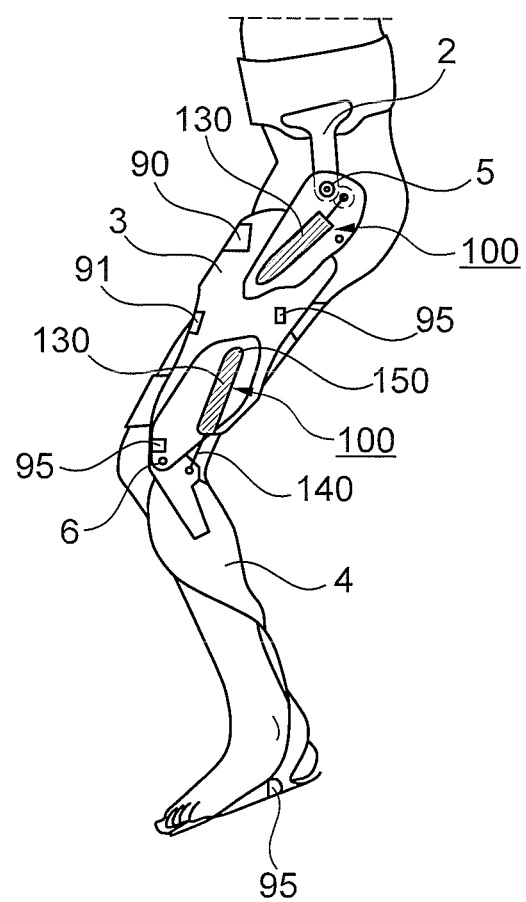
FIG. 4 is a schematic depiction of an application example in accordance with the present disclosure.

An example of an embodiment of the present disclosure is illustrated in FIG. 4, in which an orthosis for the lower limb is depicted. The orthosis is fixed to the torso of the patient via a hip belt or hip connection 2. An upper leg shell 3, which can be attached to the upper leg via straps acting as fixing devices, is attached to the hip connection 2 via a joint axis 5. Via the swivel axis 6, a lower leg shell 4 with a footrest is flexibly mounted on the upper leg shell 3, wherein it is mounted distally to the upper leg shell 3. A total of two hydraulic actuators 100 are provided, each of which is arranged between an upper part and a lower art of the orthosis. The hydraulic actuator 100 is fixed between the hip connection 2 and the upper leg shell 3 in such a way that, upon a swivelling about the swivel axis 5, the piston rod 140 retracts into or extends out of the housing 130. Correspondingly, a second hydraulic actuator 100 is mounted, along with the housing, on the upper leg shell via the bearing accommodation 150 and on the lower leg shell or the lower leg part 4 via the piston rod 140 and the mounting point. In this case, a swivelling about the swivel axis 6 also leads to a relative movement between the piston rod 140 and the housing 130, and thus to a movement of the piston 160 inside of the housing 130. Sensors 95, such as pressure sensors, acceleration sensors, force sensors or angular sensors, are arranged on the orthosis, the sensors being coupled with the control device 85. In the example of an embodiment shown, an operating element 90, for example in the form of a touch screen, is also arranged on the upper leg shell 3; via the operating element, it is possible to operate the control device 85 and therefore the motor drive 80 in order to adjust the preload of valve 1. In addition, a communication interface 91 is arranged on the orthosis, on the upper leg shell 3 in the example of an embodiment shown, in order to, for example, to run a software update via a central control device, or to record data and energy and transfer it to the orthopedic device with the hydraulic unit, or to run a data analysis.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. For example, any of the features of any given embodiment disclosed herein may be used with any other embodiment. The embodiments were chosen and described in order to best explain the principles of the present systems and methods and their practical applications, to thereby enable others skilled in the art to best utilize the present systems and methods and various embodiments with various modifications as may be suited to the particular use contemplated.

Unless otherwise noted, the terms "a" or "an," as used in the specification and claims, are to be construed as meaning "at least one of" In addition, for ease of use, the words "including" and "having," as used in the specification and claims, are interchangeable with and have the same meaning as the word "comprising." In addition, the term "based on" as used in the specification and the claims is to be construed as meaning "based at least upon." Throughout this disclosure the term "example" or "exemplary" indicates an example or instance and does not imply or require any preference for the noted example. Thus, the disclosure is not to be limited to the examples and designs described herein but is to be accorded the widest scope consistent with the principles and novel features disclosed herein.

The invention claimed is:

1. An orthopedic device comprising:
a hydraulic damping device;
a valve having a valve seat and a valve body, the valve body being subjected to a closing force along a direction of displacement, the closing force being applied via a valve spring that is pre-loaded towards the valve seat parallel to or along the direction of displacement;
a valve spring holder that is coupled with the valve spring, wherein the valve spring holder is mounted in a housing and a first thread is configured on the valve spring holder, the first thread engaging with a second thread, which is arranged in the housing;
a fluid connection between the hydraulic damping device and the valve seat; and
an adjustment device for adjusting the pre-load of the valve spring, wherein the adjustment device is formed separately from and attached to the valve spring holder, and wherein the valve seat is adjustably positioned within the hydraulic damping device to adjust the pre-load of the valve spring, and wherein the valve seat is adjustable parallel to or along the direction of displacement.

2. An orthopedic device according to claim 1, wherein the adjustment device comprises a screw drive.

3. The orthopedic device according to claim 1, wherein the pre-tension force on the valve body is infinitely adjustable.

4. The orthopedic device according to claim 1, wherein the adjustment device comprises adjustment markings.

5. The orthopedic device according to claim 1, wherein the adjustment device comprises a positive-locking element, the positive-locking element configured to activate the adjustment device.

6. The orthopedic device according to claim 1, wherein the adjustment device comprises a motor drive and a control device that is coupled with the motor drive for controlling the motor drive.

7. The orthopedic device according to claim 6, further comprising an operating element that is coupled with at least one of the control device and a communication interface for controlling the motor drive.

8. The orthopedic device according to claim 6, wherein the orthopedic device comprises at least one sensor, which is coupled with the control device.

9. The orthopedic device according to claim 8, wherein the control device is configured to adjust the spring pre-load depending on at least one sensor value.

10. The orthopedic device according to claim 9, wherein the control device is configured to at least one of:
determine the body weight and a value of a parameter of a movement by at least one sensor;
to calculate at least one control parameter for the drive from the determined value or values; and
to automatically activate the drive to adjust the pre-load of the valve spring.

11. An orthopedic device comprising:
a hydraulic damping device;
a valve comprising:
a valve seat;
a valve body, the valve body being subjected to a closing force along a direction of displacement;
a valve spring that is preloaded towards the valve seat and configured to apply the closing force parallel to or along the direction of displacement, wherein the valve body comprises a first bolt configured to at least partially retain the valve spring;
a valve spring holder that is coupled with the valve spring, the valve spring holder comprising a second bolt configured to at least partially retain the valve spring, wherein the valve spring holder is mounted in a housing and a first thread is configured on the valve spring holder, the first thread engaging with a second thread, which is arranged in the housing; and
an adjustment device to adjust the preload of the valve spring, wherein the adjustment device is formed separately from and attached to the valve spring holder, and wherein the valve seat is adjustably positioned within the hydraulic damping device to adjust the pre-load of the valve spring, and wherein the valve seat is adjustable parallel to or along the direction of displacement; and
a fluid connection between the hydraulic damping device and the valve seat.

12. The orthopedic device according to claim 11, wherein the adjustment device comprises a screw drive.

13. The orthopedic device according to claim 11, wherein the pretension force on the valve body is infinitely adjustable.

14. The orthopedic device according to claim 11, wherein the adjustment device comprises adjustment markings.

15. The orthopedic device according to claim 11, wherein the adjustment device comprises a positive-locking element, the positive-locking element configured to activate the adjustment device.

16. The orthopedic device according to claim 11, wherein the adjustment device comprises a motor drive and a control device that is coupled with the motor drive to control the motor drive.

17. The orthopedic device according to claim 16, further comprising an operating element that is coupled with at least one of the control device and a communication interface to control the motor drive.

* * * * *